United States Patent [19]
Zacouto

[11] Patent Number: 5,306,293
[45] Date of Patent: Apr. 26, 1994

[54] DEVICE FOR THE PREVENTION OF CARDIAC FAILURES

[76] Inventor: Fred Zacouto, 16 rue de la Convention, 75 015 Paris, France

[21] Appl. No.: 796,250

[22] Filed: Nov. 21, 1991

[30] Foreign Application Priority Data

Nov. 23, 1990 [FR] France .................. 90 14643

[51] Int. Cl.⁵ .............................................. A61N 1/36
[52] U.S. Cl. ............................... 607/17; 607/19; 607/21; 607/22; 607/23; 607/24; 607/25; 607/26
[58] Field of Search ............. 128/419 PG; 607/9, 17, 607/18, 19, 22, 25, 26, 23, 21, 24

[56] References Cited

U.S. PATENT DOCUMENTS

| | | | |
|---|---|---|---|
| 3,857,399 | 12/1974 | Zacouto | 128/419 P |
| 4,052,991 | 10/1977 | Zacouto | 128/419 PG |
| 4,473,078 | 5/1982 | Angel | 128/419 D |
| 4,552,150 | 11/1985 | Zacouto | 128/419 PG |
| 5,053,008 | 10/1991 | Bajaj | 128/24 AA |

FOREIGN PATENT DOCUMENTS 0387363  3/1989  European Pat. Off. .
0348271  6/1989  European Pat. Off. .
1237702  6/1960  France .

*Primary Examiner*—Lee S. Cohen
*Assistant Examiner*—Jeffrey R. Jastrzab
*Attorney, Agent, or Firm*—Larson & Taylor

[57] ABSTRACT

The implantable device, of the Holter intervention type, permits the detection and the polygraphic analysis (ECG, TA, haemodynamics, resonant frequencies), of the cardiovascular parameters, especially in the active sequence of current cycles, permitting the instantaneous activation of a cardiac electrical or neurovegetative or pharmacological stimulation. The device comprises automatic adaptation means permitting the active permanent monitoring of the hearts treated, repaired by prosthesis (especially valvular, arterial or myocardial), or repaired by transgenic tissue graft (including a graft in the presence of specific growth factors such as FGF).

18 Claims, 2 Drawing Sheets

DEVICE FOR THE PREVENTION OF CARDIAC FAILURES

BACKGROUND OF THE INVENTION

The invention relates to a device for the prevention, on the one hand, of disorders of the cardiac rhythm, especially ventricular tachyarrhythmia or tachycardia, and ventricular fibrillations, which are the cause of sudden death, and, on the other hand, mechanical cardiovascular insufficiencies, thrombosis and haemorrhages.

RELATED ART

The automatic treatment of cardiac disorders by means of implanted devices exhibits essentially a momentary palliative or curative aspect, without preventing relapses or treating the cause. The first cardiac pacemakers were designed to make up for the insufficiencies of the cardiac electrogenesis, especially in the case of bradycardia due to auriculo-ventricular block. The automatic treatment of tachycardia or of tachyarrhythmia, especially ventricular, proved to be difficult, and it was necessary to await the invention of the orthorhythmic pacemaker (U.S. Pat. No. 3,857,399 and U.S. Pat. No. 4,052,991 Paris 1970) by the Applicant in order to succeed in automatically reducing, with good prospects of success, tachycardia or tachyarrhythmia. The curative action of this device, which intervenes upon detecting an incipient tachyarrhythmia or tachycardia, also exhibits, to a certain extent, a preventive aspect, since it frequently prevents a detected tachycardia from continuing sufficiently to become hazardous. Nevertheless, it continues to be desirable to be able to prevent any inception of tachycardia. It is for this reason that recent years have seen the development of a large number of defibrillators based on the automatic defibrillation invented by the Applicant (FR-A-1,237,702 of 11.7.1953) and intended to detect selectively the occurrence of a ventricular fibrillation and to generate a defibrillation electric shock.

The Applicant has already sought to develop devices for the prevention of acute cardiac crises. One of these devices, which is described in the Patent U.S. Pat. No. 4,552,150 (1983), periodically tests the excitability of the myocardium by emitting infraliminal pulses, which are not normally followed by any response, in order to undertake a regulation of the myocardium by electrical stimulation when the excitability threshold falls to an excessive extent.

Another device designed by the Applicant in the Patent Application EP-A-0,384,271 (Paris 1988) permits the detection of risks of sudden thrombosis or sudden ischaemia, for example of the coronary arteries, which are the cause of myocardial infarction and of postischaemic lesions, in order to initiate a medicinal action.

SUMMARY OF THE INVENTION

The invention proposes to remedy these disadvantages and to provide a device for the prevention of sudden cardiac failures and of mechanical cardiac insufficiency and which permits the prevention, in a large number of cases, of the occurrence of ventricular extrasystoles, of ventricular tachycardia or tachyarrhythmia, and of ventricular fibrillations, as well as failure due to cardiac insufficiency or thrombosis or haemorrhage.

A further object of the invention is to provide such a device which continues to be effective in a very wide range of clinical situations, including haemopathy and disorders of blood coagulation.

A further object of the invention is to provide such a device which can be constructed from conventional electronic components which have been employed for a great length of time in implanted systems.

Yet a further object of the invention is to provide such a device which improves the orthorhythmic pacemaker which is already known.

Yet a further object of the invention is to provide such a device which can readily be associated, in combination, with already known devices and especially cardiac pacemakers, defibrillators, implanted devices for haemodynamic support, anti-ischaemic devices, etc.

The subject of the present invention is a device for the prevention of cardiac and blood disorders, especially sudden failures, ventricular arrhythmia and cardiac insufficiencies, comprising:

means for the detection of cardiac and/or blood parameters, means for cardiovascular intervention and/or alert, characterized in that in addition to the detection of the occurrence of severe cardiac disorders, it comprises:

storage means sensitive to said detection means and capable of retaining, at least temporarily, in memory, the succession of the parameter values corresponding to an active sequence of cardiac cycles, and comparison means, permitting the comparison of said succession of parameter values of said active sequence with previously stored information concerning parameter values and, in the event of positive comparison, the initiation, prior to the occurrence of the disorder, of the preventive activation of said intervention and/or alert means.

The device according to the invention may be arranged, for example, with the aid of a program, about a microprocessor connected to memory elements. This means may incorporate:

the conventional logic means for the acquisition of the parameter values from the sensors which detect them, as well as shaping and, where appropriate, filtering; these means are already employed in implanted devices for detecting and analyzing signals, for example electrocardiographic signals or other parameters such as, for example, intravascular pressure, ion or chemical concentration, etc.;

comparison means, incorporating for example threshold values with which detected parameter values are compared;

if required, logic means, which are likewise already conventionally employed and which are preprogrammed to decide that the result of the comparison constitutes the diagnosis of a severe disorder necessitating the activation of the alert and/or cardiac intervention means; these means are already conventionally employed in pacemakers and in implantable cardiac defibrillators.

These means which, in their initial form, were wired and constructed by discrete electronic circuits, are now generally constructed in programmed form in association with a microprocessor and its conventional environment and these devices are generally available commercially.

The device further comprises, according to the invention, means permitting the storage of the succession of the parameter values corresponding to the active sequence of cardiac cycles which has just been detected;

means which have stored at least one succession of earlier values constituting the previously stored information to decide, where appropriate, on the preventive activation of the intervention and/or alert means.

Of course, these comparison means may be essentially the same, just as the memories retaining the active sequences and the previously stored information may be essentially the same as those aforementioned, the invention then being performed by the logical activation of these means.

In a particularly preferred embodiment, the means described hereinabove are wholly or partly self-programmable in such a manner as to permit the adaptation of the device to the natural development of the cardiovascular condition or to the developments, on the one hand, of prostheses placed at the location of the heart and, on the other hand, of autologous or heterologous tissue grafts with cells whether genetically modified or not, in a manner which is autonomous with respect to the predetermined programming.

This self-learning, which may be established by making use of conventional software for artificial intelligence, may be arranged to be able to modify, in particular, at least one of the following elements, in particular in their logical form:

sensitivity level of the sensors as well as parameter value identification logic;

modification of the previously stored information concerning parameter value or, while retaining the previously stored information, storage of other acquired information, for example the successions of the parameter values of sequences which have actually occurred and which, having preceded the occurrence of a cardiac disorder, were then stored in a permanent manner, so that the active sequence of cardiac cycles which has just been detected will be compared not with a series of previously stored information but with a plurality of series of previously stored information;

accounting for modifications originating from the subject's own activity by detection of this activity;

accounting for a progressive or rapid modification of the condition of the cardiac muscle, of blood coagulation and of other physiological conditions;

modifications of the automatic treatment delivered by the cardiac intervention means, in their intensity, their sequence or in the nature of drugs which are automatically delivered.

Within the meaning of the invention, an active sequence of cardiac cycles is understood as referring to a sequence of cardiac cycles which are preferably directly consecutive, which sequence has just terminated, or which slightly precedes the instant of said comparison.

Thus, preferably, the active sequence of cardiac cycles is the sequence constituted by the last n cardiac cycles which have just taken place at the instant under consideration, the number n preferably ranging 6 and 8 and a few hundreds or thousands (sic). However, it is likewise possible to use sequences of very long duration, of the order of a plurality of hours to a plurality of days, i.e. tens of thousands to millions of cycles. Thus, for example, in a preferred embodiment, the active sequence is the sequence of the last 72 cycles which have just taken place. In such a construction, on each occasion that a new cardiac cycle is detected, this new cycle forms part of the active sequence and the oldest cycle is eliminated therefrom so that n remains constant.

However, although this is not preferred, the active sequence could also be constituted by a non-constant number of cycles, for example all the cycles which took place during a specified period, for example ranging between 30 seconds and 120 minutes, prior to the instant of the comparison.

In a further variant, the active sequence may be constituted by a sequence of cycles which does not terminate immediately by the current cycle but which terminates prior to the current cycle at the specified instant.

According to the invention, said storage means retain in memory the set of ordered values corresponding to the parameter(s) measured during the active sequence.

Within the meaning of the invention, a cardiac parameter is understood as referring to any detectable, measurable or calculable parameter giving information on the cardiovascular condition and/or the condition of the blood.

These parameters may be of electrical type, that is to say the acquisition of which is capable of being performed by means such as electrodes or sensors, in particular cutaneous, subcutaneous, juxtacardiac, intracavital, intramyocardial, pericardial or intravascular. Among these parameters, the following are in particular preferred:

cardiac period and frequency, cycle by cycle, for example the interval RR, form of the electrocardiogram, vectocardiogram, QRS complexes, in particular amplitude and morphology, interval of the T wave (for example the QT value), form and/or propagation of the T wave, gradient of the T wave, vectocardiogram, detection of delayed QRS potential, endocavital, ventricular or auricular impedances, transparietal impedances, impedances within the vena cava, and within the thoracic duct, platelet aggregation and activation (determined, for example, by optical detections), selective activation of the lymphocytes (antigen-antibody links)

coagulant and/or anticoagulant factors, fibrinogenesis and fibrinolysis factors.

The stored values of these parameters, at each cycle, may be the actually measured or detected values of a parameter. However, it is understood that it is likewise possible, on the basis of the measured values, to create values calculated as a function of the various parameters or of the analysis of a complex parameter. In particular, where use is made of one of the parameters relating to the T wave, it is possible to utilize the ratio of the QT interval of the current cycle to the value of the RR cycle, for example the immediately preceding one, the current one or the one to come.

Said parameters, referred to as electrical parameters, may, in an extremely simple embodiment, be detected between two electrical points, for example between a right intracavital electrode and an electrode carried at the surface of the casing of an implanted device according to the invention. However it is preferred, in the invention, to detect the parameters, for example the electrovectocardiogram, by measurement between at least three reference points, in a manner known per se, this being so in particular in the case where use is made, by way of parameter, of the duration, the form or the amplitude of the QRS or T waves or complexes, or the shift, the orientation and the dispersion of these waves along the various geometric directions of the measurement reference system.

The detection may be performed in an original manner which does not trace the simple resultant of the electric vectors of the left and right ventricles but, on the contrary, observes separately the vector paths of or within each ventricle at each cycle in order to be able to detect the propagations and critical intervals of each ventricle. To this end, use is made of at least one endocavital electrode in the right ventricle and preferably likewise in the left ventricle, preferably in a parietal position. In this way, the small insulated endocardiac electrodes connected in single-pole configuration in relation to epicardiac, juxtacardiac or subcutaneous electrodes, permit the recording of the endocardiac potentials.

Conversely, this device, according to a variant of the invention, permits the simultaneous or successive switching of the endocardiac electrodes into the position of electrical continuity with each other and with the blood medium (by electrical connection with the metallic casing of the cardiac pacemaker and an auricular electrode, for example) and the simultaneous switching of the insulated epicardiac or juxtacardiac or cutaneous electrodes into a single-pole position. In the last-mentioned manner, the epicardiac potentials are obtained. The simultaneous or successive alternate acquisition of the epicardiac and endocardiac potentials on the same axes or vectors permits a very precise measurement of the AQRS and AT transparietal gradients; this opens up the area of the very early ECG detection of ischaemia or other myocardiac lesions—even mild and quiescent ones—together with their localization, which is necessary for the automatic prevention of cardiac failures by analyzed internal polygraph records and instantaneous selective intervention.

The device may also perform electrophysiological tests which have been employed up to the present time for generating ventricular tachycardia after programmed extrastimuli, this taking place by means of extrastimuli with orthorhythmic intervals of coupling (in terms of percentage or in terms of milliseconds) to analyze the cardiovascular, haemostatic and other polygraph reactions (especially ECG, QT and AT, QRS durations, gradients and dispersions, cardiovascular mechanograms and other parameters).

The device may include, held in memory, information which is programmed or, or in a variant. acquired during operation, concerning the normal modifications of the parameters under the effect of effort or emotion and upon return to the resting condition, it being necessary to avoid confusion of these modifications with pathological modifications. This identification is performed by multiple means for detection of force which are already known in VVIR-type cardiac pacemakers and storage in a special register.

Other electrical parameters which are measured or calculated may be:
the number or percentage and morphology of the ventricular extrasystoles, as well as their RR' coupling interval,
the surface area, obtained by integration, of the QRS complexes and/or of the T waves,
the duration or form of the T waves.

Preference is given, especially in the case where detections are performed on a plurality of geometric axes in such a manner as to be able to use as parameter not only the measured electrical absolute values but also the temporary shifts which may occur on the various axes, to the determination, by a means known per se, of the direction of the electric axis of the heart at the instant of the measurement. It is, in fact, known that the electric axis of the heart, which may vary pathologically in the event of a heart attack, also varies temporarily as a function of the respiratory cycle or of the postural position of the person connected to the device according to the invention. The instantaneous acquisition of the direction of the electric axis of the heart may be obtained, for example, by comparison of the signals obtained on various leads, for example D1, D2 and D3 of the heart.

It is however understood that other cardiac, blood or cardiovascular parameters may be detected and utilized in the invention, for example chemical parameters such as oxygen or $CO_2$ saturation, pH, lactic acid, alpha or beta myosin, catecholamines, endothelin, concentration of tone such as $K^+$, $Ca^{++}$, $Na^+$, content of certain coagulant, anticoagulant, fibrinogenic or fibrinolytic factors, content, present in the myocardium, of glutathione or other antioxidants, of toxic free radicals or mechanical parameters such as duration or ratios of the isovolumetric concentration (PEP), pressure diagram or pressure-volume diagram, volume of the heart, value of the ejection pressure, derivative dP/dt of the pressure, integral of the pressure (pressure.time) per cycle, etc.

Thus, the device may prevent the establishment of a vascular haemorrhage or thrombosis by making use of means capable of detecting in situ the functional condition of the blood coagulation, by making use, for example, of a device described by the inventor in EP-A-0,348,271 and of injecting immediately by means of known implantable pumps, substances, for example thrombin inhibitors comprising small molecules such as, for example, D/N-methyl-phenylglycyl-Pro-arginal 0.5 mg/kg and/or hirudin 0.25 mg/kg, and/or aspirin 0.02 g or alternatively an inhibitor of factor XIII, such as a derivative of iodacetamide (for example fluoracetamide, 1 mg). Such an inhibition of thrombin, without any risk of haemorrhage, may be sufficient to exercise sufficient control over the natural intrinsic tPA potential to dissolve the blood clot in the course of formation; if this is not the case, the blood coagulation detector of the inventor records the new spontaneous fibrinolysis wave and the apparatus may then automatically inject a very low dose of a thrombolytic agent.

After its dissolution or stabilization at minima for thrombosis, a return of the latter may be avoided by the selective alarm given by the remote control of the implanted device which warns the bearer and advises the intake of a suitable anticoagulant.

The intravascular detection device permits awareness of the commencement of the formation of fibrin in another vessel by using the biochemical equivalent (EP-A-0,348,271) of a small permanent wound around which the fibrinolysis/fibrinogenesis balance switches over to an intense and rapid fibrinolysis which is observable and is characteristic of a thrombosis of a certain severity. Depending upon whether the thrombosis is or is not dissolved, the fibrinolysis ceases or continues, permitting a distinction to be drawn between the cessation and non-cessation of the thrombosis, the signalling thereof to a monitor and instructions for the continuance or noncontinuance of the automatic administration of a medicament to be given.

Advantageously, the device may comprise an implanted optical sensor, such as an illuminating, orientable and cleanable microcamera, which is currently available, in an intracardiac position and capable of visualizing a part of the heart on the cellular, intercellular and infracellular scale.

In order to measure with precision the movements and dimensions of the cardiac cavities and walls, the device may likewise comprise a miniature orientable intracardiac probe for ultrasonic emission and reception, the signals of which are processed by the implanted microcontroller.

Another parameter of interest may be the value of the arterial pressure, which may be measured, for example, by amplification of the acoustic or infraacoustic spontaneous vibrations at the resonant frequencies of the arterial tree. Where appropriate, these vibrations may be caused by low frequency endocavital acoustic emission or acoustic pulse, the deformations and the attenuation of which are proportional to the pressure in the arterial tree.

In a variant, the analysis of the resonant frequency, especially of the systolic noise detected on or near a ventricular wall, permits the monitoring of its contractile function.

The detection of the resonant frequencies of the valvular, myocardial, arterial or aortic cardiac prostheses permits the monitoring of these prostheses.

The parameter values may be acquired at each cycle of the active sequence, or only at certain cycles, for example 1 cycle in 10 or according to a different selection, for example 1 cycle in 500, these selections moreover possibly being different from one parameter to another over time, depending upon the condition of detection of each parameter and from one parameter to another within one and the same sequence.

Of course, the device may be arranged to undertake exploratory or diagnostic tests by causing variations of the parameters, for example by electrical stimulation at programmed intervals (for example investigation of inhibition of ventricular extrasystoles by slight acceleration of the stimulation rhythm), or by action of pharmacological, chemical or biological products.

The results of these tests may then advantageously be used within the context of a self-learning program, either for modifications of the comparison logic as a function of the developmental trends of the pathological or physiological parameters, or for modifications of the treatment, for example variation in intensity of the electrical stimulations or of the doses of medicaments.

Within the meaning of the invention, a means of cardiac intervention is understood as referring to any means permitting the prevention of the appearance of ventricular tachyarrhythmia, tachycardia or extrasystoles, or of sudden failures or of a mechanical insufficiency. These means may comprise implanted means such as micropumps, permitting the delivery of a drug, for example, into the blood or into the myocardium or a partial or total haemodynamic support, for example, provided in Patent Application EP-A-0,348,271. However, in the simplest embodiment, these means may be electrical stimulation means of a conventional type permitting the emission of one or more stimulation pulses with a possibly high potential, sufficient to resynchronize the cells of the myocardium.

By way of example, the intervention means may comprise peripheral electrodes, for example subcutaneous electrodes, at two opposite points of the thorax to generate infraliminar electrical stimulation pulses for the cardiac muscle, but which are sufficient to stimulate the neurovegetative system, especially in the event of excessive stability of the RR period in the active sequence, possibly associated with a diminution of the mechanical reactions under the effect of effort or after injection of hypertensives.

Within the meaning of the invention, the comparison means are comparison means of the logic type and which are preferably implantable, being articulated, for example, about a microprocessor.

In a first embodiment of the invention, the device according to the invention retains in memory the values of the parameters of at least one former sequence, concerning which it is known that it has been followed by a cardiac event, for example bradycardia, ventricular tachycardia or ventricular tachyarrhythmia, ventricular fibrillation or cardiac arrest, or indeed concerning which the physician considers that it is associated with a risk of mechanical failure. These values may have been input once and for all into the apparatus and stored in the latter but, in an improved embodiment, these values may have been and continue to be acquired automatically by the device according to the invention, which is then arranged to retain permanently in memory the succession of the values of the parameters of the sequence of n (for example 72) cycles which have been followed, immediately, or preferably, after an interval, by the event, for example the tachycardia or fibrillation or purely mechanical failure of the myocardium or a sudden fibrinolysis or fibrinogenesis. In such an embodiment, the apparatus is arranged not only to store the active sequence but also to retain, whether or not indefinitely, the former active sequence which, directly or indirectly, preceded the event.

Means are provided for cancelling former critical sequences, for example after pharmacological, genetic or surgical treatment.

According to the invention, said comparison means compare the succession of parameter values of the active sequence which they have just acquired with the succession or successions of values of the hazardous former sequences which have been automatically stored or programmed. In the event of similarity between these compared successions, the apparatus initiates the activation of the intervention means, for example electrical stimulation means, and/or an alarm received on an extracorporeal receiver.

Within the meaning of the present invention, similarity is understood as referring to a certain degree of resemblance between the parameters of the two sequences and it is possible to refer in this instance to techniques close to the known techniques of image analysis permitting a decision that an image resembles another on the basis of a certain degree of similarity without a perfect coincidence being essential. Thus, by way of example, if the parameter is constituted simply by the measurement of the cardiac rhythm, it may be imagined that the device will be arranged so that it considers that there is similarity not only in the case of similarity, to an accuracy of a predetermined percentage, for example 4%, with the absolute values of the various cycles, but also in the case of resemblance of analogical or homothetic type of the two sequences, or indeed of significant parts of these sequences.

According to the invention, and especially in the case where the apparatus is arranged itself to detect and store the hazardous sequences which have actually preceded an event, it will be preferred not to initiate the intervention at the very last moment but, on the contrary, before this stage This may be done, for example, in the case where n is equal to 36, by retaining in memory, for example, a sequence of 72 cycles immediately prior to the occurrence of the event and by comparing the active sequence with the first 36 cycles of the hazardous sequence stored.

In a second embodiment of the invention, which is applicable especially, but not exclusively, to the case where one of the principal parameters relates to the T wave, the succession of values of the parameter of the active sequence is compared not with a succession of values of a sequence which preceded a hazardous event, but, on the contrary, with information relating to values or developments considered as normal for the patient and it is decided that the comparison is positive, that is to say initiates the alert or the intervention of, for example, the stimulating means, when the parameter values of the active sequence differ significantly from said information. Thus, for example, if the succession of parameter values is constituted by the ratio QT/RR (where RR may be the duration of a cycle of the QT interval in question, or indeed in a variant, the duration of a preceding cycle), a determination is made, either before the positioning of the apparatus or directly by the apparatus itself, of the function, normal for the patient, of the variations of said ratio QT/RR and the stimulation is undertaken if, in the course of the active sequence, the measured curve of this function differs by at least a certain magnitude or predetermined percentage from the customary curve for the patient.

Of course, the first and second embodiments of the invention may be combined in the same device.

Irrespective of the embodiment, the apparatus may further comprise comparison means which are instantaneously sensitive to a sudden variation, that is to say a variation which is virtually instantaneous, of a parameter in order to initiate an immediate intervention. For example, the apparatus may incorporate the whole or part of the means of the orthorhythmic device previously described in the aforementioned US-A patents.

In a general way, the device is arranged to discriminate the parameter values on separate memories, depending upon whether they originate from a spontaneous, electrically stimulated or merged rhythm.

For example, a significant and instantaneous diminution of the length of the RR cycle will be considered as an extrasystole and a stimulation intervention will take place immediately after a programmed interval. Alternatively, for example, a rapid modification of the QT shift in one of the electrical detection leads of the electrocardiogram in relation to another lead (for example V1, V5) will be able to cause an immediate response of the device, whether or not during the same cycle.

The device according to the invention is preferably of the implantable type and, in this case, it is preferred that it comprises, in addition to the means for the detection and acquisition of the parameter values, which may possibly be of a conventional type, and the stimulation intervention means, which may likewise possibly be of a conventional type, storage means of any type and a central processing unit executing the computations and comparisons and managing the operation of the whole, for example adaptation to the physiological changes of the rest-effort type, such as, for example, a microprocessor. Where the device is implanted, it further comprises a power source, for example an electrical battery.

Where the device according to the invention is implanted, it may advantageously comprise means for remote transmission from and to the implanted device. These means are already in current use in implanted pacemakers and do not need to be detailed. They are arranged to permit the remote command or remote programming, remote alarm and/or remote monitoring, preferably with remote display on a monitor, especially for the purpose of monitoring the correct operation of the parameter sensors and of the microprocessor, of undertaking automatic tests of diagnostic and therapeutic effectiveness, and of reprogramming new definitions of active sequence, of comparison criteria and of developmental trends. They may likewise be used to transmit the reactions to tests monitoring the effect of chemical or other medications.

Furthermore, the remote control means may be arranged to be able to give instructions from the outside for the automatic and immediate intravascular administration of predetermined doses of medicament (for example trinitine), including administration by the patient himself and, in the event of persistence of pain, the automatic administration of thrombin inhibitors or low doses of fibrinolytic or other agents. Thus, the device may comprise, in association with or entirely independent of the remainder of the invention, implantable means for the distribution of very low doses of at least one medicament in the blood circulation, for example an automatically controlled pump. Preferably, this device permits the delivery of thrombin inhibitors, especially of small peptides such as (D) N-methyl-phenylglycyl-Pro-argynal or other similar products, or alternatively of hirudine. The dose of a short peptide inhibitor of this type is preferably of the order of 0.1 to 1 mg per kg body Preferably, the device may likewise comprise a means for the administration of a coronary vasodilator such as trinitrin or its derivatives for an administration of a very low dose, for example of the order of 10 mg. Preferably, the device may comprise, in addition to the means for the administration of thrombin inhibitor, a source for the delivery of a dose of aspirin and/or a source for the delivery of a fibrinolytic agent in a very low dose such as TPA, for example in a single dose of 10 to 20 mg. The remote control casing, especially where this is intended to be used by the person carrying the device himself, may advantageously comprise a plurality of commands, such as, for example, buttons, where appropriate associated with a release system, preferably one command or pushbutton per type of medicament. In the case of patients for whom there is a risk of coronary thrombosis, the manually operable device may advantageously be provided to impose the following order: voluntary administration of trinitrin, followed by a waiting period of a few minutes - voluntary administration of a dose of thrombin inhibitor, followed by a period of several minutes, and then, in the case where this source is present, voluntary administration of the very small dose of fibrinolytic agent. It is possible to provide that the device authorizes the voluntary delivery, at a minimum interval of several minutes, of trinitrin or of thrombin inhibitors. Thus, the patient will be constrained to commence, in the event of pains being experienced, by the administration of at least one dose of trinitrin and then, if the pain does not cease, the administration of a dose of inhibitor and then, if the pain persists and if the apparatus includes the relevant feature, the administration of a dose of fibrinolytic agent. In the case of non-coronary patients who are at risk of non-coronary thrombosis, for example pulmonary or cerebral trombosis, the device for the distribution of trinitrin will not be present or supplied.

Preferably, this device is associated with means for the acquisition and interpretation of the electrocardiogram, which means may be of an entirely conventional type, making use of a microprocessor to analyze the electrocardiogram and to detect the existence of a variation which may reflect a coronary thrombosis or a pulmonary embolism so that the administration of the inhibitor or of the fibrinolytic agent will be authorized only after positive electrocardiographic detection of this thrombosis. In the preferred embodiment, the device is associated with the other means described in the invention permitting the prevention of cardiac and/or blood disorders, including the permanent monitoring of the coagulation factors.

Thus, for example, the physician may take the conventional measurement of blood pressure by armband and obtain the values, at this instant, of multiple parameters corresponding to this pressure, especially dp/dt, PEP, QRS integral, integral of the segment ST, systolic volume, diastolic volume, transparietal impedance of the myocardium, etc... By measuring pressures of differing values, which are possibly caused at different instants, it is thus possible to construct an abacus of blood pressure which, when stored in the device, will permit at each instant an automatic computation of this pressure which will form one of the parameters utilized in the apparatus.

In a variant of the measurement of blood pressure, it is likewise possible to utilize the fine analysis of the form of the intraventricular pressure curve, which is likewise an indication of the pressure.

The device may likewise be external and, in this case, it may comprise a computer of any type, possibly with peripherals such as a keyboard, screen and printer, as well as the detection and stimulation means with the required analogue/digital interfaces, optoelectronic coupling means possibly being interposed, for the electrical safety of the subject, between the parts connected to the body, such as the sensor, electrodes and stimulation means and the remainder of the device.

The subject of the invention is also the process for the treatment of the heart consisting in detecting cardiac or blood parameters, in storing, at least temporarily, the succession of the parameter values corresponding to a sequence of parameter values, to previously stored information concerning parameter values and, in the case of positive comparison, in initiating the activation of cardiac or blood alert or intervention means.

The effective prevention of cardiovascular failures may provide for a constant adaptation to the development of the new therapeutic possibilities. The latter comprise A- partial or total cardiac tissue grafts and B- partial or total artificial hearts and C-treatment of the pathological substrates.

A - Tissue grafts of cardiac tissues taken from the patient and genetically repaired, and then multiplied in vitro and controlled prior to selective reimplantation in the heart of the patient, where his renewed cells ensure progressively, by their growth, the repair of the heart. In certain cases, the genetic repair may be performed by simple injection of exogenous genes which are capable of obtaining their expression by gene transfer, for example the cardiac myosin gene.

B - Intracardiac graft of foreign natural cardiac tissues, for example embryonic, natural or transgenic; in the latter case, chromosomes or groups of genes of the embryonic cells are taken and replaced, for example by corresponding genetic elements of the subject and for example strengthened by anti-infection genes in order to improve the tolerance and the functioning, after in vitro multiplication, of the grafted tissue which will multiply and will progressively replace in situ the former diseased or old cardiac cells.

C - The reconstitution in vitro of a complete ventricular personal heart, from autologous or homologous tissues which are genetically repaired, improved and controlled, and possibly associated with a framework or mechanical structures.

These partial or total tissue grafts or reconstitutions making use of genetically repaired cells will probably progressively replace conventional cardiac grafts, the survival of which is frequently remarkable but limited in time, even if only as a result of intracardiac atherosclerosis and immunosuppressive treatments.

In a variant, the invention is applied to these hearts subjected to reconstitution by repaired cells which may have serious disorders of the rhythm or failures due to mechanical insufficiencies or haemodynamic excess. In these cases, the invention will utilize analyzed cardiovascular multiple detections, the software for which will be programmed and will program itself while taking account of the functioning and of the normal development of the repaired heart.

The use of partial or total implanted artificial hearts (concerning which the first experimental investigation with survival of the animal was published by the author together with Coraboeuf and Monod et al. C.R. Soc. Biol. January 1956, T:150, pages 48-51) will give impetus to a variant of the present invention, since an artificial heart, whether it be regulated to a rhythm, volume or systolic pressure, whether constant or not, undergoing adaptation to effort, will cause a reaction of the arterial and venus tree of the neurovegetative system and a blood hypercoagulability. In the event of a detected thrombosis hazard, a preventive injection which is automatic or initiated by remote control, of thrombin inhibitor may be performed. Under these conditions, in order to avoid a "collapse or failure" of the artificial heart by excessively strong dilation of the capillaries and of the veins or hazardous arterial spasms, the monitoring and the preventive regulation of an artificial heart becomes a new application of the invention. The measured parameters will preferably be the central and arterial venus pressures and, in the event of detection of a reduction in venus pressure, the device gives a command instruction to the artificial heart, for example to reduce the rate of flow and to avoid the collapse or to administer a drug such as adrenalin.

A variant of the invention is applied to hearts, the general condition of which is still satisfactory but only a part of which constitutes a very pathological substrate, for example an ischaemia, necrosis or localized fibroblast degeneracy producing deceleration and deviation of the activation and myocardial repolarization, a source of ventricular tachycardia. In this case, the device of the invention will detect and localize the diseased substrate in the healthy myocardium. This detection may advantageously be performed by detection of the electrocardiographic modifications, by modification of the regional form of the T waves and of the duration QT and of the gradient AT, as well as a mechanical anomaly (increase in the PEP and diminution of dp/dt, of the systolic volume and of the FE ejection fraction).

The device may initiate either an alarm on a remote monitor with an indication of the detected parameters of the diseased substrate, displaying, for example, left anterior local ischaemia, the need for intervention, or itself proceed by means of an implanted minipump with blood perfusion, for example of certain fibroblast growth factors (FGB) which are capable of initiating a revascularisation and a reimplantation of normal myocardial cells in the zones affected by ischaemia or necrosis.

It is also possible to inject cells which are genetically capable of revascularising and recolonizing the myocardium into the diseased substrate by catheterisation.

The invention is also applied, in an advantageous manner, to hearts carrying valvular, vascular or ventricular prostheses, as well as to hearts which have been transplanted or which receive tissue grafts.

Preferably, in all these cases, the device will incorporate an artificial intelligence logic program so as to adapt its operation to the physiological or physiopathological development. For example, this might be effected by detection and known evaluation of the systolic and diastolic function which would permit, for example, the progressive modification of the comparison means.

BRIEF DESCRIPTION OF THE DRAWINGS

Further advantages and features of the invention will become evident upon reading the description which follows, which is given by way of non-limiting example and which refers to the accompanying drawings, in which.

DETAILED DESCRIPTION

Figure 1:
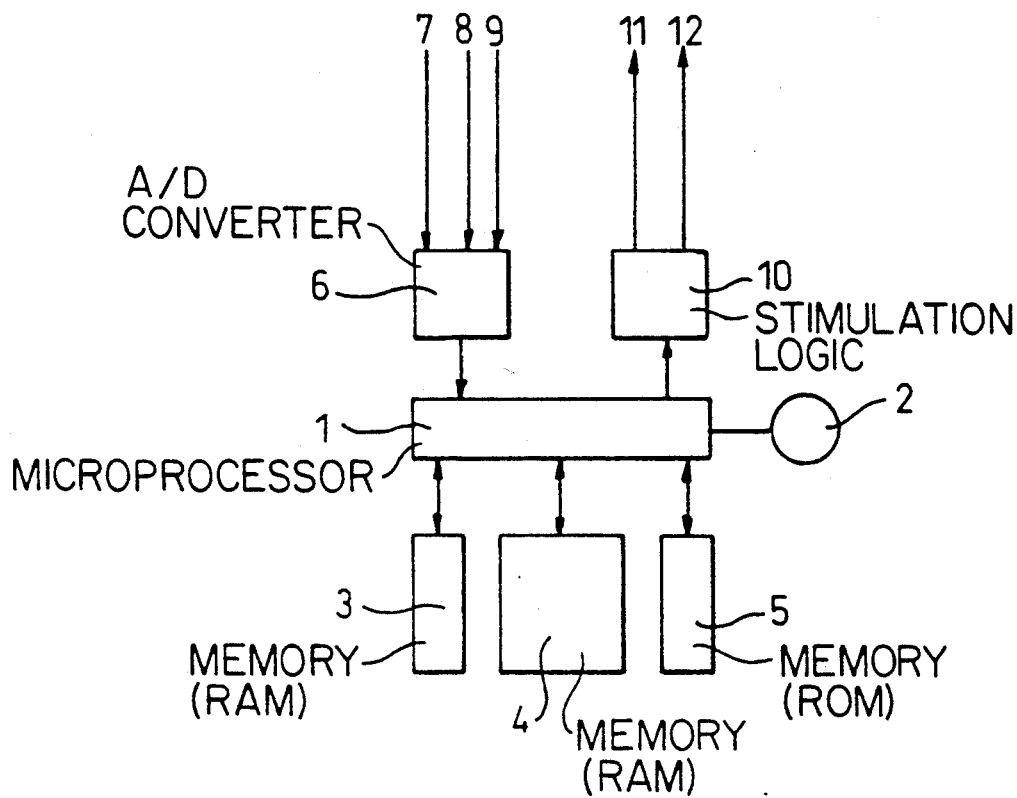
FIG. 1 represents a view, in the form of a functional block diagram, of an implantable device according to the invention.

The implantable device according to the invention, represented in FIG. 1, comprises a central processing unit 1 such as a microprocessor, to which are added a source of electric current 2 and memories such as a memory 3, preferably of RAM type, which is intended to store the current active sequence, a memory 4, preferably of RAM type, intended to store the successions of parameters of a plurality of sequences, for example a sequence input by programming and one or more sequences which may take place and which are followed by a cardiac event detected by the device, as well as a memory 5, preferably of ROM type, comprising instructions for the general operation of the microprocessor 1. Other additional memories may possibly comprise other information such as, for example, information relating to the patient, to his illness and its development, to the physiological modifications as well as information relating to the type of intervention, for example power intensity, and localization and orientation of the electrical stimulations, etc. The microprocessor 1 is furthermore connected to an analogue/digital conversion unit 6 to which there passes, via appropriate implanted conductors, the information from various sensors 7, 8, 9 such as detection electrodes, pressure sensors, etc. Finally, the central unit 1 is connected to a stimulation logic 10, for example of a known type, capable of undertaking the treatment of the heart, by the emission of stimulation pulses, activating actuators such as 11 and 12, for example stimulation electrodes. The assembly of the components 1-6, 10 is contained in a sealed casing of the same type as those utilized in implanted cardiac pacemakers, which casing may itself carry, for example, an electrode leading to the converter 6.

EXAMPLE 1

Figure 2:
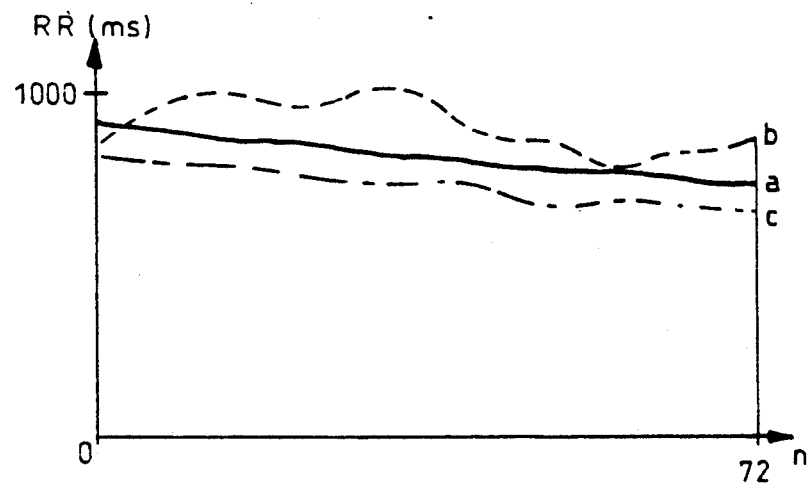
FIGS. 2 and 3 represent curves of parameter values which are employed in the device.

FIG. 2 shows, for a specified patient, the curve of parameter values of a sequence which the physician considered to be hazardous for the patient following a study on a HOLTER recording.

The parameter is the RR period of the cardiac cycle. The curve a in FIG. 2 represents the development of the period of the cardiac cycles during 72 consecutive cycles. As may be seen, this development is characterized on the one hand by a high degree of constancy of the RR ratio in which the RR interval of two consecutive cycles differs by less than 5%, as well as by a general trend towards a very progressive diminution of the duration of the RR interval. The curve thus established is stored in the memory 4.

12 cycles after the end of the sequence represented, the patient had undergone a ventricular tachycardia detected on HOLTER.

The microprocessor retains constantly in the memory 3 the similar curve b formed by the values of the RR intervals of the last 72 cycles detected, that is to say of the active sequence.

At each cycle, the microprocessor 1 compares the curve b of the active sequence which has just been reupdated in the memory 3 with the curve a which is recorded in the memory 4.

Thus, for example, the active curve b, which is represented in FIG. 2, differs from the curve a by rhythm variations which on occasions exceed 5%, as well as by fluctuations of increase and of diminution. This sequence is not considered to be hazardous.

Curve c shows a sequence which is considered to be hazardous and which is characterized both by a trend towards acceleration and by very small differences, less than 5%, between two consecutive RR intervals.

In the case where this active sequence of 72 cycles continues, the comparison with the sequence a is positive and the microprocessor 1 then commands the emission of a series of stimulation pulses by the device 10, at a rhythm which is slightly above the spontaneous rhythm and with a power of four times the threshold.

EXAMPLE 2

The active sequence comprises 1152 cycles on this occasion.

The device employed in this example comprises a plurality of endocavital and subcutaneous electrodes arranged, in a manner known per se, so as to obtain the electrocardiogram on a plurality of geometric leads. The microprocessor is programmed to determine, from the signals received on the various electrodes, the following parameters:

RR interval (a1), detection and count of the ventricular extrasystoles identified by their morphology, duration and propagation, RR' coupling interval of the extrasystoles, that is to say the interval between one extrasystole and the earlier QRS complex (a3), percentage (a2) of ventricular extrasystoles, this percentage, detection of the T wave and duration of the QT interval (a4), dispersion (a5) of the QT interval, that is to say the difference, within the same cycle, between the durations of the QT intervals in a, for example, anterior left ventricular lead in relation to the parietal and the posterior.

The device further includes a right intraventricular pressure sensor permitting the formation of the value of the PEP (a6) and likewise, by the microprocessor, the computation of the variation of the pressure dp/dt (a7).

It further includes logic means computing the surface area of the pressure mechanogram (a8), a detector of the partial pressure of oxygen (a9) and an endocavital sensor for blood pressure (a10).

According to the invention, the device measures and computes these various parameters at each cycle which takes place and retains the values of the last 1152 cycles, that is to say of the active sequence, in the memory 3.

In fact, in the example represented, the device retains in the memory 3 the sequence of the parameter values of the last 9216 cycles; this, of course, includes the last 1152 cycles.

Moreover, the microprocessor is programmed so as to be able to establish the occurrence of a cardiac failure. For example, the device considers that a level of at least 15% of identified ventricular extrasystoles indicates a failure, just like the detection of a ventricular fibrillation. The association of electronic detection means and means for detecting the pressure of the heart is already described in the literature, for example French Patent FR-A-1,237,702.

When the device according to the invention, which is preferably combined with an automatic defibrillator and with an antitachycardia device as described in the U.S. Pat. No. 4,052,991, detects the occurrence of a cardiac failure, it extracts from the memory 3 the values of the parameters corresponding to the 9216 cycles which preceded the occurrence of the failure and inputs them into the memory 4.

Figure 3:
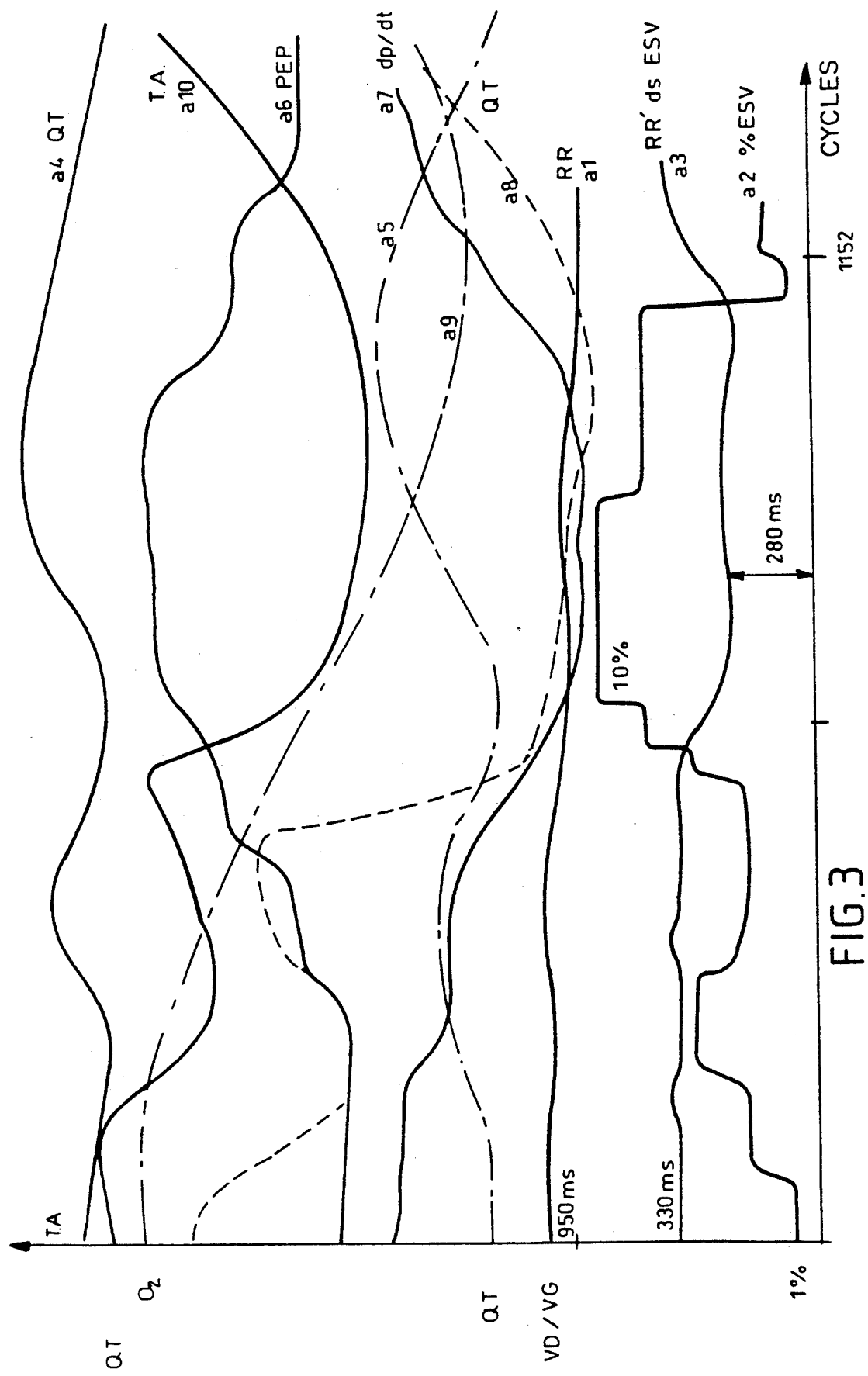

FIG. 3 shows the curves 1 to 10 of the various parameters in the course of a sequence of 1152 consecutive cycles constituted by the cycles 1252 to 100 which preceded the occurrence of the failure.

The device according to the invention permanently compares the values of the various aforementioned parameters during the current active sequence with the values stored and represented on the curves (a1 ... a10) of FIG. 3.

For the curve a1 (RR), the comparison is made as in Example 1.

For the curve (a2) (percentage of extrasystoles), the device estimates that there is resemblance in the comparison as soon as a close number of extrasystoles has been counted during the sequence.

In the case of the curve (a3) (RR' of the ventricular extrasystoles), it estimates that the curves resemble one another if a plurality of extrasystoles having an RR' coupling interval below 350 ms have been detected.

With regard to the curve (a4) (QT interval), it estimates that the curves resemble one another if they exhibit the same amplitudes and rates of growth.

With regard to the curve (a5) (dispersion of the QT interval), it estimates that the curves resemble one another if the variations of the dispersion, in the two curves, are greater than 50 ms and the QT dispersion/QT minimum duration ratio varies significantly.

Comparison criteria are possibly retained for the curves (a6 to a10).

The microprocessor is programmed in the following manner:

the positive comparison of the curves (a1) does not bring about the intervention of the device unless the comparison of at least one of (a2, a3, a6 and a7) is positive.

On the other hand, a coincidence of the curves (a2) and/or (a3) will involve the activation of the intervention means of the device without requiring that at least one of the other curves coincides with the corresponding curve of the active sequence.

In the example which has just been described, the active sequence is compared with the sequence shown in FIG. 3, which has been stored and which corresponds to the cycles 1252 to 100 prior to the failure which has been recorded.

In fact, in a variant, it is possible to compare the active sequence with a large number of earlier stored sequences and, it would be possible for example to compare the active sequence with any one of the sequences formed by 1152 consecutive cycles, the last one of which is selected in an arbitrary manner among the cycles stored in the memory 4.

In a further variant, the device may be arranged, by programming of the microprocessor, in such a manner as to retain as stored comparison sequence one of the sequences of 1152 consecutive cycles, which sequences have occurred prior to the recorded failure and exhibiting a particularly characteristic form, for example a large number of ventricular extrasystoles, a prolongation of the QT and a significant shift of the QT intervals on two different leads giving an abnormal QT dispersion.

With regard to the ventricular extrasystoles, the device is, as has been stated, preferably combined with the means for reducing tachycardia which are described in the aforementioned US patent application. This process detects the occurrence of a certain number of extrasystoles or an incipient tachycardia and automatically gives rise to an isolated stimulation, or preferably to a sequence of electrical stimulations, at a frequency which is greater than that of the extrasystoles which have just been detected. At the end of the stimulation, the device according to the invention detects whether the extrasystoles are or are not persisting. If the extrasystoles are not persisting, the device may be arranged so as not to involve the activation of the intervention means.

If, on the other hand, the extrasystoles persist, the alert and/or intervention means are then automatically activated.

I claim:

1. A device for the prevention of a cardiac failure, said device comprising:
sensor means for detecting at least one cardiac parameter including a parameter from which a cardiac cycle is inferred,
logic processing means, responsive to said sensor means, for determining a parameter value from said at least one parameter,
first memory storage means, controlled by said processing means, for storing a succession of said parameter values corresponding to an active sequence of cardiac cycles, and
second memory storage means for permanently storing parameter values of at least one former sequence which has been followed by a detected cardiac failure, said processing mans comprising comparison means for comparing said succession of said parameter values, corresponding to said active sequence of cardiac cycles, with said permanently stored information, and said device further comprising intervention means, responsive to said comparison means, for delivering a preventive treatment in response to a result of said comparison if said result corresponds to predetermined values.

2. Device according to claim 1 wherein said second storage means automatically stores said former sequence at the instant when said detected cardiac failure is detected.

3. Device according to claim 1 wherein said comparison means is responsive to a similarity between said succession of said parameter values of the active sequence and of said former recorded sequence which preceded a cardiac failure in order to activate said intervention means in response to a verification of similarity.

4. Device according to claim 1, wherein said second memory storage means stores parameter values which are considered to be normal for a patient connected to the device, and said comparison means compares said succession of said parameter values of the active sequence with said normal parameter values to provide initiation of the intervention means when there is a significant difference between said succession of said parameter values of the active sequence and said normal parameter values.

5. Device according to claim 1 further comprising electrodes to detect electrical parameters, said processing means determining from said electrical parameters at least one parameter selected from the group consisting of: cardiac period and frequency (RR), amplitude, morphology and form of an electrocardiogram, vectorcardiogram, QRS complex, interval of a T wave (QT), form of a T wave, propagation of a T wave, gradient of a T wave, vectorcardiogram of a T wave, QT wave dispersion, detection of delayed QRS potential, impedances, number of percentage of morphology of ventricular extra-systoles, RR' coupling intervals of ventricular extra-systoles, duration of the QRS complexes and duration of T waves.

6. Device according to claim 5 further comprising vectographic detection means for detection of a heart vectographic electrocardiogram.

7. Device according to claim 6, wherein said vectographic detection means comprise endocavital means in at least one ventricle to separately detect a vectographic electrocardiogram of said ventricle.

8. Device according to claim 5, wherein said parameter values of said succession are related to each cycle of said active sequence.

9. Device according to claim 1 further comprising sensor means, of a chemical type, for sensing at least one parameter selected from the group consisting of oxygen or $CO_2$ saturation, pH, lactic acid, concentration of ions, including $Ca^{++}$, coagulation factors, antioxidants, myosin, catecholamines, endothelin and free radicals.

10. Device according to claim 9, wherein said parameter values of said succession are related to each cycle of said active sequence.

11. Device according to claim 1, further comprising at least one pressure sensor said processing means being coupled to said at least one pressure sensor and determining therefrom at least one of the following values: PEP, dP/dt, pressure diagram, pressure/volume diagram, volume of the heart, value of the ejection fraction, and integral of the pressure.

12. Device according to claim 11, wherein said parameter values of said succession are related to each cycle of said active sequence.

13. Device according to claim 1, further comprising effort of a patient detection means for the detection of effort and for producing an output in accordance therewith, said processing means being responsive to the output of said effort detection so as to modify said comparison means based on said output.

14. Device according to claim 1, further comprising means for the detection of at least one parameter selected from the group consisting of coagulant, anticoagulant, fibrinogenic and fibrinolytic factors.

15. A device for the prevention of a cardiac failure, said device comprising:

sensor means for detecting at least one cardiac parameter, including a parameter from which a cardiac cycle is inferred, logic processing means, responsive to said sensor means, for determining a parameter value from said at least one parameter, first memory storage means, controlled by said processing means, for storing a succession of said parameter values corresponding to an active sequence of cardiac cycles, and second memory storage means for permanently storing parameter values of at least one former sequence which has been followed by a detected cardiac failure, said processing means comprising comparison means for comparing said succession of sad parameter values, corresponding to said active sequence of cardiac cycles, with said permanently stored information, and said device further comprising alarm means, responsive to said comparison means, for producing an alarm in response to a result of said comparison if said result corresponds to predetermined vales.

16. Device according to claim 15, further comprising remote control means, which can be actuated externally by a person carrying the device, for permitting, upon demand, self-administration by said person of appropriate medicaments.

17. A device for the prevention of a cardiac failure, said device comprising:

sensor means for detecting at least one cardiac parameter including a parameter from which a cardiac cycle is inferred, logic processing means, responsive to said sensor means, for determining a parameter value from said at least one parameter, first memory storage means, controlled by said processing means, for storing a succession of said parameter values corresponding to an active sequence of cardiac cycles, and second memory storage means for permanently storing parameter values which are considered to be normal for a patient connected to the device, said processing means comprising comparison means for comparing said succession of said parameter values, corresponding to said active sequence of cardiac cycles, with said normal parameter values, and said device further comprising intervention means, responsive to said comparison means, for delivering a preventing treatment when there is a significant difference between said succession of said parameter values of said active sequence and said normal parameter values.

18. A device for the prevention of a cardiac failure, said device comprising:

sensor means for detecting at least one cardiac parameter including a parameter from which a cardiac cycle is inferred, logic processing means, responsive to said sensor means, for determining a parameter value from said at least one parameter, first memory storage means, controlled by said processing means, for storing a succession of said parameter values corresponding to an active sequence of cardiac cycles, and second memory storage means for permanently storing parameter values which are considered to be normal for a patient connected to the device, said processing means comprising comparison means for comparing said succession of said parameter values, corresponding to said active sequence of cardiac cycles, with said normal parameter values, and said device further comprising alarm means, responsive to said comparison means, for producing an alarm when there is a significant difference between said succession of said parameter values of said active sequence and said normal parameter values.

* * * * *